United States Patent [19]

Ikeda

[11] Patent Number: 5,028,441

[45] Date of Patent: Jul. 2, 1991

[54] EDIBLE MATERIAL CONTAINING MUSHROOMS

[76] Inventor: Hisakazu Ikeda, 4210-82, Sakaki, Oaza, Sakaki-machi, Hanishina-gun, Nagano 389-06, Japan

[21] Appl. No.: 397,577

[22] Filed: Aug. 23, 1989

[30] Foreign Application Priority Data

Aug. 30, 1988 [JP] Japan ................................ 63-217399

[51] Int. Cl.⁵ .............................................. A23L 1/28
[52] U.S. Cl. ...................................... 426/49; 426/52; 426/53; 426/61; 426/62; 426/615; 426/7; 426/60; 426/46
[58] Field of Search ....................... 426/44, 46, 49, 52, 426/53, 61–62, 615, 7, 60

[56] References Cited

FOREIGN PATENT DOCUMENTS

| 0020433 | 6/1978 | Japan | 426/49 |
| 0181671 | 11/1982 | Japan | 426/52 |
| 0095859 | 6/1984 | Japan | 426/52 |
| 0226476 | 11/1985 | Japan | 426/52 |

*Primary Examiner*—Marianne Cintins
*Attorney, Agent, or Firm*—Burgess, Ryan & Wayne

[57] ABSTRACT

An edible material is produced from grassy materials such as corncob, the husks of rice, barley or buck-wheat etc. by cultivating a fungus of edible mushrooms in a medium containing the grassy material to have the medium digested and removing the specific odor therefrom by heating or fermenting the digested medium. The edible material is nutritious, has good odor and can be served as feed to animals.

3 Claims, No Drawings

EDIBLE MATERIAL CONTAINING MUSHROOMS

BACKGROUND OF THE INVENTION

1. Field of the Invention

This invention relates to an edible material obtained by processing a digested medium resulted from the cultivation of mushrooms. The material can be used as a food for animals and human.

2. Description of the Prior Art

Main feed for domestic animals is cereals which are also food for humans, and, grasses which can not be eaten by human are generally used as feed for ruminants.

In order to reduce the cost of feed, husks such as rice husks and corncob etc. are used partially as crude feed for ruminants, however, it has not been used widely because good results are not obtained. Most of the husks are being disposed of.

Furthermore, with respect to a material obtained by decomposing a waste medium resulted from the cultivation of mushrooms in a medium containing mainly sawdust by the action of yeast etc., there have been conducted feeding tests by research organizations and farmhouses in each place.

However, the tests in most cases encountered large obstacle in continuous feeding. For example, in the case of feeding the above material to twenty cattle, very satisfactory growth was observed for 7 months, but, thereafter, the animals lost their appetites rapidly, exhibited robot-like actions by the stiffening of muscles and all of them came to die within one month.

The reason is not yet clarified, but it seems that resins, tar and cyanic compound etc. originated from the sawdust were probably accumulated in the animal's body and the hindrance appeared when the accumulation had increased beyond some level.

In order to overcome the above problem, present inventor has carried out many years of research for cultivating mushrooms employing grass materials avoiding woody materials such as sawdust.

It has been found that good result is obtained when the digested medium yielded from the above cultivation is improved in the taste by employing the medium in a small amount under adding thereto the lees of soybean sauce or apple juice, molasses, compound feed etc. However, when the ratio of the medium to the additives is increased, the feed declined in taste and no good result is obtained.

Furthermore, in the case of employing a digested medium obtained by the cultivation of mushrooms as a feed, a long period of time is consumed to accustom animals to the feed, therefore, the conversion of feed requires complicated procedures, and the digested medium is not suitable for human food because of its odor.

SUMMARY OF THE INVENTION

The present invention intends to solve the problems, and provides an edible material which comprises a digested medium obtained by cultivating a fungus of mushrooms in a medium wherein finely cut grassy material which is rich in lignin is combined with nutrient sources, having the specific odor of the medium removed therefrom.

DESCRIPTION OF THE PREFERRED EMBODIMENTS

As the grassy material being rich in lignin, there may be exemplified, for instance, rice husks, barley husks, corncob, bagasse, the husks of buck-wheat or soybean, stems or leaves of *Gramineae* etc. These materials are employed as a cut form having a volume density of preferably about 0.15 to 0.66.

As the nutrient sources, it is preferable to employ materials such as rice bran, wheat bran, soybean-curd lees (residue left after pressing soybean milk out of boiled soybean). If desired, grain powder such as rice powder, wheat flour, soybean powder may be employed.

When the nutrient sources are calculated as dry materials containing 10% of water, the ratio by weight of the above cut grass material to the nutrient sources may preferably be about 3-4:2 in weight.

As the mushrooms to be cultured, any of edible mushrooms which can be cultivated, such as Enokitake (*Flammulina veltipes*), Hiratake (*Pleurocus ostreatus*), Bunashimeji (*Hypsizygus marmoreus*), Maitake (*Grifola frandosa*), Nameko (*Pholiota nameko*) and Shiitake (*Lentinula edodes*) may be employed.

The cultivation of mushrooms can be carried out by conventional manners employed in mushroom cultivation. For example, in the case of Enokitake, a medium is filled into bottles and sterilized by heating. On the medium, the fungus of Enokitake is inoculated and cultivated at 20° C. for 20 to 30 days, and then the surface of the medium is scrape out to expose new surface. After allowing to stand at 10° C. for 8 to 10 days, the fruit bodies of Enokitake grown in banks 2-3 cm in height is wrapped with papers to protect from toppling over and after further several days, matured fruit bodies are harvested.

In the cases of other mushrooms, their cultivation may be carried out depending on the kind of mushroom by a conventional or known method or a method similar thereto.

By the above cultivation, hyphae are grown in the medium and the ingredients of the medium are digested and decomposed with enzymes secreted from the hyphae.

In present invention, mushrooms are cultivated to digest their culture mediums and the harvest of fruit bodies has only subsidiary meaning. Therefore, as far as the medium is digested, the harvest of the fruit bodies may be omitted and any fungus of the mushrooms may be cultured, if it is harmless in food sanitary.

The digested medium thus obtained has a specific odor like a decayed fruit body of a mushroom, and the odor is removed in present invention.

The removal of the odor can be carried out by heating the digested medium.

The temperature of the heating is preferably not less than 70° C. and, if desired, a temperature around 100° C. or more may be employed.

Suitable time required for the heating depends on the heating temperature. For example, it is 1 to 2 hours at around 100° C.

The digested medium is sterilized simultaneously with deodorization by heating, therefore, it can be preserved, and further it can be dried by heating to make a dried material.

The heating may be carried our directly by fire or indirectly by atmospheric or high pressure steam.

The removal of odor from the digested medium can be carried out by fermenting the medium.

In the fermentation, the digested medium may be employed as it is or after sterilization by heating.

The fermentation is carried out by fermenting the medium under addition of a microorganism harmless in food and sanitary.

As the microorganism, there may be exemplified, for instance, a yeast belonging to *Torula, Saccharomyces, Schizosaccharomyces* etc., a fungus belonging to *Aspergillus, Mucor*, etc., and a bacteria such as a lactic-acid bacteria belonging to *Lactobacillus, Streptococcus, Bacillus*, etc. and *Bacillus natto* etc. Among them, particularly preferable is a yeast for making Sake (Japanese rice wine), beer or bread, *Aspergillus oryzae*, a lactic-acid bacteria, *Bacillus natto* etc.

Each of these microorganisms can be employed solely or as a mixture thereof.

The fermentation is carried out generally at around 20° C. to 40° C. When sufficient heat generates by the fermentation, there is no need for take the trouble to heat.

Thus, if the fermentation is carried out sufficiently, the specific odor of the digested medium is removed and, in most cases, an aroma by the fermentation occurs.

When the digested medium deodorized as above is given to domestic animals, it can be almost completely ingested showing very high ingestion rate. Accordingly, a large amount of crude protein and other nutrient sources contained in the medium are utilized effectively. Therefore, employing it as a concentrated nutrient, the healthy fattening of warm-blooded animals such as domestic animals can be planned. It is also suitable as a feed for a cold-blooded animals such as fishes and the like. Furthermore, it can be used as a food for human, because it is rich in nutrients, its bad odor has been removed and excellent results have been obtained in the fattening tests of domestic animals.

The present food material can be employed, if desired, in combination with other feed, bait or food, depending on the animal to be fed.

The deodorized digested medium may be used as it is, however, from the view point of handling, it is generally preferable to preserve in a dried form and it may be processed to the powder or pellets of the dried material.

According to present invention, an edible material rich in nutrients and applicable to wide field as feed, bait and food is provided, employing digested mediums resulted from the cultivation of mushrooms in mediums consisted mainly of agricultural waste.

Hereinafter, present invention is further explained in the form of examples.

EXAMPLE 1

50 g of corncob, 40 g of rice husks and 30 g of the husks of buck wheat were cut respectively to make each 0.22 of volume density and mixed each other. To the mixture, 150 g of soybean-curd lees, 50 g of wheat bran and 10 g of rice bran were added as nutrient sources, and the water content of the mixture was adjusted to 63%. The adjusted mixture was filled into bottles of 800 ml each in volume as culture medium whereon Hiratake was cultivated.

The fruit bodies of Hiratake thus grown were yielded and the residual digested medium was dried by heating in a drying room.

In the drying room which had been converted from a vinyl house for drying grass, room temperature elevated to about 80° C. making use of radiant heat by the direct irradiation of the sun. The digested medium was placed in containers for nursery bed and spread to thin layers, and then the containers were placed on a draining board in the drying room, and heated by sun light in the daytime of fine weather for 2 days.

The dried material thus obtained lost the bad odor and became to have an aroma like to concentrated feed. The dried material as it was tried to feed to pigs, sheep and cattle. The animals ate up the material willingly and there was no need of adding other feed or tasty material at all.

EXAMPLE 2

Each 20 kg of the digested material obtained in the same manner as in Example 1 was filled in vinyl bags each which was placed on shelves in an atmospheric steam sterilizer so as not to be piled up each other and heated for 2 hours by steam until the fire of burner for generating the steam was extinguished, followed by allowing to stand for 1 hour.

The heat-treated, digested medium thus obtained became to have an aroma like boiled rice, and, when it was fed to pigs, sheep and cattle, the animals ate up it willingly as in the product of Example 1.

EXAMPLE 3

150 Kg of digested medium obtained in the same manner as in Example 1, 30 kg of molasses for feed (a feed product for cattle containing molasses; produced by Fuji Shiryo Co., Ltd.), 10 kg of rice bran and 6 kg of Vitakogen (a special feed containing lactic-acid bacteria, *Bacillus subtilis*, yeast, *Aspergillus oryzae* etc.; produced by Seiwa Sangyo Co., Ltd.) were mixed each other, and the water content of the mixture was adjusted to 50%. Then the mixture was heaped on a floor and covered with a mat. It was summer and the temperature of the open air was 30° C. After 1 hour, the mixture began to ferment and after 10 hours the temperature of the mixture rose to 45° C. and then gradually fell to 25° C. after 20 hours.

The medium thus treated occurring sweet and sour aroma was filled in vinyl bags and stored.

EXAMPLE 4

A digested medium was prepared in the same manner as in Example 1, excepting that materials consisting in the ratio of 80 g of corncob, 40 g of rice husks, 200 g of soybean-curd lees and 50 g of wheat husks were employed and the water content is adjusted to 64%.

On the medium, a mushroom was cultivated as described in Example 1 to give a digested medium. To 200 kg of the digested medium, 100 kg of a compound feed for piglets (Meiji Highmax, produced by Meiji Milk Products Co., Ltd., Tokyo) and 5 kg of Biopremix (a preparation containing *Bacillus natto*, Lactic-acid bacteria, yeast and *Aspergillus oryzae*; produced by Matsumoto Microbiology Research Co., Ltd., Matsumoto) were added and mixed each other. Each 20 kg of the mixture was filled in vinyl bags each and subjected to fermentation. The atmospheric temperature was 27° C. After 3 days, the fermented material was able to feed to piglets, and as not less than 7 days passed, it became to occur very sweet and sour aroma and showed increased taste to piglets.

EXAMPLE 5

An experiment was carried out in the same manner as Example 4, except for employing yoghurt instead of Biopremix, to obtain results similar to Example 4.

In the above Examples 3 to 5, small amounts of nutrient sources for the fermentation are required, however, the bad odor of the digested medium was replaced by the aroma of the fermentation and came to show very increased ratio of ingestion.

I claim:

1. An edible material which comprises a digested medium obtained by cultivating a fungus of edible mushrooms in a medium comprising a grassy material selected from the group consisting of rice husks, barley husks, corncob, bagasse, buck-wheat husks, soybean husks, and the stems or leaves of *Gramineae* and a nutrient source selected from the group consisting of rice bran, wheat bran and soybean-curd lees; said grassy material being in a cut form having a volume density of 0.15 to 0.66; and having the specific odor of said digested medium removed therefrom by heating the medium at about 70° to 100° C. or by fermenting the medium with *Torula, Saccharomyces, Schizosaccharomyces, Lactobacillus, Aspergillus,* or *Bacillus natto* microorganisms.

2. An edible material as claimed in claim 1 wherein the heating of the digested medium has been carried out by steam at a temperature not less than 95° C.

3. A method for producing an edible material which comprises cultivating a fungus of edible mushrooms in a medium comprising a grassy material selected from the group consisting of rice husks, barley husks, corncob, bagasse, buck-wheat husks, soybean husks, and the stems or leaves of *Gramineae* and a nutrient source selected from the group consisting of rice bran, wheat bran and soybean-curd lees; said grassy material being in a cut form having a volume density of 0.15 to 0.66; recovering the medium digested by the cultivation; and then removing the specific odor of the digested medium by heating the medium at about 70° C. to 100° C. or fermenting the medium with yeast, *Lactabacillus, Aspergillus,* or *Bacillus natto* microorganisms.

* * * * *